(12) United States Patent
Minamida et al.

(10) Patent No.: US 9,180,653 B2
(45) Date of Patent: Nov. 10, 2015

(54) PREPREG PRODUCTION METHOD

(75) Inventors: Daiki Minamida, Ehime (JP); Koichi Kawase, Ehime (JP); Osamu Kuramata, Otsu (JP); Takashi Mori, Ehime (JP); Keita Oe, Ehime (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 14/354,443

(22) PCT Filed: Aug. 28, 2012

(86) PCT No.: PCT/JP2012/071664
§ 371 (c)(1),
(2), (4) Date: Apr. 25, 2014

(87) PCT Pub. No.: WO2013/061682
PCT Pub. Date: May 2, 2013

(65) Prior Publication Data
US 2014/0299253 A1 Oct. 9, 2014

(30) Foreign Application Priority Data
Oct. 28, 2011 (JP) ................... 2011-236952

(51) Int. Cl.
*C08J 5/24* (2006.01)
*G01N 21/88* (2006.01)
(Continued)

(52) U.S. Cl.
CPC ............... *B32B 41/00* (2013.01); *B29C 70/506* (2013.01); *B29C 70/54* (2013.01); *B32B 7/06* (2013.01);
(Continued)

(58) Field of Classification Search
CPC . C08J 5/24; B32B 2305/076; G01N 21/8422; G01N 21/88; G01N 21/8806; G01N 21/8851; G01N 21/89; G01N 21/8901; G01N 21/892; G01N 21/8921; G01N 21/94; G01N 2021/8472; G01N 2021/8841; G01N 2021/8854; G01N 2021/8861; G01N 2021/8874; G01N 2021/888; G01N 2021/8908; G01N 2021/8925
USPC ........ 156/64; 356/237.1, 238.1, 238.2, 238.3, 356/237.2, 237.3
See application file for complete search history.

(56) References Cited

U.S. PATENT DOCUMENTS 7,171,033 B2 * 1/2007 Engelbart et al. ............. 382/141
2011/0135872 A1 6/2011 May et al.

FOREIGN PATENT DOCUMENTS

| EP | 2 226 624 A1 | 9/2010 |
| JP | 06-228340 A | 8/1994 |

(Continued)

OTHER PUBLICATIONS

Machine Translation of JP 2010-085166 A. Fukuzawa et al. Date of Publication Unknown.*

(Continued)

*Primary Examiner* — Michael Tolin
(74) *Attorney, Agent, or Firm* — RatnerPrestia (57) ABSTRACT

Provided is a method of producing prepreg including: inspecting, with an optical device, in a resin sheet made of a release paper and a resin film which is formed by coating the release paper with a resin to be impregnated into a carbon fiber bundle, the surface of the resin film, detecting a defect in the surface of the resin film which would be the cause of a defect in the prepreg to be produced, and judging the type of the detected defect; or inspecting, with an optical device, the surface of the prepreg after the release paper is separated from the prepreg sheet which is formed by impregnating a resin forming the resin film into the carbon fiber bundle, detecting defects in the surface of the prepreg, and judging the type of the detected defect.

8 Claims, 2 Drawing Sheets

(51) Int. Cl.
*G01N 21/892* (2006.01)
*B32B 41/00* (2006.01)
*G01N 21/898* (2006.01)
*G01N 21/84* (2006.01)
*G01N 21/94* (2006.01)
*B29C 70/50* (2006.01)
*B29C 70/54* (2006.01)
*B32B 7/06* (2006.01)
*B32B 29/02* (2006.01)
*G01N 21/89* (2006.01)

(52) U.S. Cl.
CPC . B32B 29/02 (2013.01); C08J 5/24 (2013.01); G01N 21/8422 (2013.01); G01N 21/88 (2013.01); G01N 21/8806 (2013.01); G01N 21/89 (2013.01); G01N 21/892 (2013.01); G01N 21/898 (2013.01); G01N 21/8914 (2013.01); G01N 21/8921 (2013.01); G01N 21/94 (2013.01); *B32B 2041/04* (2013.01); *B32B 2250/40* (2013.01); *B32B 2255/12* (2013.01); *B32B 2255/26* (2013.01); *B32B 2262/106* (2013.01); *B32B 2305/076* (2013.01); *B32B 2305/08* (2013.01); *B32B 2305/22* (2013.01); *B32B 2307/738* (2013.01); *B32B 2307/748* (2013.01); *B32B 2313/04* (2013.01); *B32B 2363/00* (2013.01); *B32B 2377/00* (2013.01); *G01N 2021/8472* (2013.01); *G01N 2021/888* (2013.01); *G01N 2021/8841* (2013.01); *G01N 2021/8854* (2013.01); *G01N 2021/8861* (2013.01); *G01N 2021/8874* (2013.01); *G01N 2021/8908* (2013.01); *G01N 2021/8925* (2013.01)

(56) References Cited

FOREIGN PATENT DOCUMENTS

| | | | | |
|---|---|---|---|---|
| JP | 08-050105 | A | * | 2/1996 |
| JP | 09-136323 | A | * | 5/1997 |
| JP | 09-150416 | A | * | 6/1997 |
| JP | 09-225939 | A | * | 9/1997 |
| JP | 2000-017546 | A | | 1/2000 |
| JP | 2008-196059 | A | | 8/2008 |
| JP | 2010-085166 | A | | 4/2010 |
| JP | 2011-085468 | A | | 4/2011 |

OTHER PUBLICATIONS

International Search Report for PCT International Application No. PCT/JP2012/071664 dated Dec. 11, 2012.
Supplementary European Search Report Issued for Application No. EP 12 84 3361, Dated Mar. 27, 2015.

* cited by examiner

PREPREG PRODUCTION METHOD

CROSS REFERENCE TO RELATED APPLICATIONS

This is the U.S. National Phase application of PCT/JP2012/071664, filed Aug. 28, 2012, which claims priority to Japanese Patent Application No. 2011-236952, filed Oct. 28, 2011, the disclosures of each of these applications being incorporated herein by reference in their entireties for all purposes.

FIELD OF THE INVENTION

The present invention relates to a method of producing prepreg including a carbon fiber bundle and a resin impregnated into the carbon fiber bundle. More particularly, the present invention relates to a method of producing prepreg in which the prepreg is produced by detecting a defect appearing in the prepreg in the production process of prepreg and using information on the detected defect.

BACKGROUND OF THE INVENTION

Composite materials made of a reinforcing fiber and a resin are widely used for sporting or leisure goods such as fishing rods and golf shafts, and equipment for airplanes, automobiles and industries. A molding material, referred to as prepreg, formed by impregnating a resin into a reinforcing fiber sheet made of reinforcing fiber bundles arranged in one direction, or a reinforcing fiber sheet made of reinforcing fibers arranged in at least two directions, for example a reinforcing fiber cloth, is used for molding of these composite materials. The composite material is produced by laminating a plurality of molding materials and molding the resulting laminate into a desired shape.

For production of the prepreg, in general, a resin sheet including a resin sheet formed of a release paper and a resin film formed from a resin coated the release paper, that is, a resin film with a release paper, and a carbon fiber bundle or a carbon fiber sheet including a carbon fiber bundle previously impregnated with a resin are used.

The surface of the resin film of the resin sheet is opposed to at least one surface of the carbon fiber sheet, and thereby a laminated sheet including the resin sheet and the carbon fiber sheet is formed. The resin in the formed laminated sheet is impregnated into the carbon fiber bundle in the laminated sheet under heating and/or pressure to produce a prepreg sheet including the carbon fiber bundle and the resin impregnated thereinto.

There are cases where two resin sheets are used and prepreg is produced by sandwiching the carbon fiber sheet between the two resin sheets.

As the resin, usually, an uncured thermosetting resin, for example, an uncured epoxy resin is used. The resin is coated the release paper by thin-film coating to form a resin film on the release paper. The thermosetting resin usually contains a curing agent. The thermosetting resin may be used in the form of a resin mixture including a thermoplastic resin mixed for the purpose of improving performance of a composite material or for the purpose of adjusting the viscosity of the resin in the production process.

As the carbon fiber bundle, a lot of carbon fibers arranged in one direction, or a lot of carbon fibers arranged in at least two directions, for example, a carbon fiber cloth, are used.

The impregnation of the resin into the carbon fiber bundle is usually conducted by a hot melt method. The impregnation of the resin into the carbon fiber bundle is performed once, or two or more times as required. The second or later impregnation of the resin into the carbon fiber bundle is performed for a carbon fiber bundle of prepreg formed by impregnating a resin into the carbon fiber bundle formed at the previous stage.

In the production process of the prepreg, defects due to foreign matter contamination that foreign matters such as cured products of a resin and fragments of a release paper are mixed in the prepreg, or due to the defective impregnation of a resin into the carbon fiber bundle (defective transfer of a resin to the carbon fiber bundle) may occur in the prepreg. Accordingly, it is important to minimize the occurrence of these defects in the production process of prepreg or detect the defects having occurred for producing composite materials of high quality which are free of defects or have little defects.

The detection of these defects of the prepreg is desirably performed without variation and with the defects classified by the type thereof according to criteria previously set in accordance with the type of the prepreg to be produced. Further, it is also desired that the position of the detected defect in the prepreg being continuously produced can be identified, and that the position of the defect can be marked on the prepreg. If the type of the defect can be identified and the position of the defect can be identified, reworking of the defect or elimination work of the defect area is enabled, and prepreg with high quality can be produced.

Conventionally, the detection of the defect of prepreg is generally performed by visual inspection. However, the visual work has problems that not only it requires extremely high concentration power, but also it tends to vary in judgment of the defect from person to person or some defects may be overlooked.

Introduction of a technique of automation of the prepreg defect inspection, which is aimed at solving these problems or saving manpower, into the production process of the prepreg is facilitated, and various techniques are proposed for shortening the inspection time or improving the inspection accuracy.

In Patent Document 1 is proposed a method of producing prepreg and an apparatus in which defects of the prepreg appearing in the production process are detected by classifying them into a fuzz defect, a gap defect and a foreign matter defect, and prepreg is produced by using the results of the detection. In this defect inspection method by Patent Document 1, the surface of the prepreg after the release paper is separated is irradiated with light to detect the defect in the surface of the prepreg. In this method, however, when a release paper is present on one surface of the prepreg, it is basically impossible to detect the defect occurred in the surface of the prepreg opposed to the release paper.

In Patent Document 2 is proposed an apparatus for producing prepreg and a method of producing prepreg in which a state of resin transfer (resin impregnation) to a reinforcing fiber bundle in the production process of the prepreg is detected, and prepreg is produced by using the results of the detection. In the inspection method of the state of resin transfer by Patent Document 2, after a resin coated a release paper is transferred to the reinforcing fiber bundle, remained resin on the surface of the release paper is inspected, and thereby, the state of resin transfer on the surface of the prepreg on a side from which the release paper has been separated is presumed. In this method, although the state related to resin transfer is detected, when a release paper is present on one surface of the prepreg, it is all the same basically impossible to detect the defect occurred in the surface of the prepreg opposed to the release paper.

In Patent Document 3 is proposed a method of inspecting defects of prepreg in which, among defects of prepreg, a gap defect and a fuzz defect are detected. However, a plurality of kinds of defects are present in the prepreg other than the gap defect and the fuzz defect, and therefore this method cannot completely save manpower and improve the inspection accuracy.

In Patent Document 4 is proposed a method of inspecting defects of prepreg in which, among defects of prepreg, a foreign matter defect, a fuzz defect, a streak defect and a wrinkle defect are detected. However, since a plurality of kinds of defects are present other than the foreign matter defect, the fuzz defect, the streak defect and the wrinkle defect, this method cannot completely save manpower and improve the inspection accuracy.

On the other hand, in the step of coating the release paper with a resin mixture to form a resin film on the release paper, the resin is partially lost on a coating roll to cause defects of resin coating that the resin is missed in the shape of a streak on the release paper, or the resin is missed in the shape of a point on the release paper.

Among these defects of resin coating, a streak-like defect may be referred to as a streak defect, and a spot defect may be referred to as a point defect. Further, foreign matters such as cured products of a resin and fragments of a release paper are sometimes mixed to cause a defect in a resin film before rolling-up a produced resin sheet. The defect due to foreign matters mixed may be referred to as a foreign matter defect.

These defects of a resin film may remain as defects in prepreg even after the resin is transferred to the reinforcing fiber bundle in the resin impregnation step of impregnating the resin into the reinforcing fiber bundle. Therefore, a criterion of the defect is defined for every kind of prepreg. Judgment of the defect is performed according to the criterion, and the position of the defect is recorded, and the defect is corrected or the defect area is eliminated from a product.

It is known to detect these defects in the production process of a resin film in which a resin film used for production of prepreg is formed.

In Patent Document 5 is proposed an apparatus for producing a resin sheet and a method of producing a resin sheet which detect a defect of a resin film formed by coating the surface of a release paper with a resin in the production process of a resin film, that is, a defect of resin coating. The defect inspection method described in Patent Document 5 is a method of detecting a defect of coating of a resin onto the surface of a resin film in the production process of a resin sheet.

However, in the production process of the resin sheet, even if a defect is detected before rolling up the resin sheet, it is basically impossible to detect a time-dependent change in the resin sheet before it is supplied to the subsequent production process of prepreg, a defect occurring in the rolling-up step of the resin sheet, or a defect occurring at the time of spreading a resin sheet from a resin sheet rolled body in the production process of prepreg, for example, a foreign matter defect occurring due to the mixing of the foreign matter.

Conventionally, usually the prepreg to which a release paper still adheres to one surface thereof, that is, prepreg with a release paper, is taken up in consideration of the handleability of prepreg when the prepreg is produced by a hot melt method. Therefore, the inspection of the defect on a surface of the prepreg on the side of the release paper is performed after separating the release paper. The release paper should be adhered to the prepreg in shipping the prepreg to a customer. However, the number of defects may be increased due to these operations, and insufficiently, only the inspection of the surface of the prepreg to which the release paper is not adhered is implemented. Accordingly, defects present on the opposite surface may be detected first upon use of the product, and remedy of this point is desired.

PATENT DOCUMENTS

Patent Document 1: JP09-225939A
Patent Document 2: JP09-150416A
Patent Document 3: JP2010-085166A
Patent Document 4: JP2011-085468A
Patent Document 5: JP09-136323A

SUMMARY OF THE INVENTION

In view of the above-mentioned problems of the prior art, the present invention aims to provide a method of producing prepreg including one or more stages of resin impregnation step(s) by a hot melt method using a release paper, which introduces an inspection technique for prepreg defects which can shorten the inspection time and improve the inspection accuracy, particularly a technique for identifying the position and the type of the defects in both surfaces of the prepreg, and a technique for transferring position information of the defect of the prepreg to the subsequent inspection step of prepreg.

A method of producing prepreg of the present invention includes the following.

A method of producing prepreg, including:

(a) at least one resin sheet supply step of continuously supplying a resin sheet made of a release paper and a resin film formed from a resin coated the release paper, (b) a carbon fiber sheet supply step of continuously supplying a carbon fiber sheet formed of a carbon fiber bundle, or a carbon fiber bundle impregnated with a resin, (c) a laminated sheet forming step of opposing the surface of the resin film supplied from the resin sheet supply step to at least one surface of the carbon fiber sheet supplied from the carbon fiber sheet supply step to form a laminated sheet including the resin sheet and the carbon fiber sheet, (d) at least one resin impregnation step of impregnating the resin in the laminated sheet in the carbon fiber bundle into the laminated sheet formed in the laminated sheet forming step to form a prepreg sheet including the carbon fiber bundle and the resin impregnated into the carbon fiber bundle, and (e) a prepreg sheet taking-up step of continuously taking up the prepreg sheet formed in the resin impregnation step, wherein the method of producing prepreg includes:

(f) at least one resin sheet inspection step of detecting a defect in the surface of the resin film which would be the cause of a defect of the prepreg by inspecting the surface of the resin film in the resin sheet supply step with an optical device and judging which of a streak-like resin missing defect, a foreign matter contamination defect and a spot resin missing defect the detected defect belongs to, or (g) at least one prepreg sheet inspection step of detecting a defect in the surface of the prepreg by inspecting the surface of the prepreg sheet with an optical device after separating the release paper from the prepreg sheet with the release paper including the release paper, which is derived from the resin impregnation step, and judging which of a carbon fiber fuzz defect, a foreign matter contamination defect, a carbon fiber bundle gap defect, a release paper wrinkle defect, a streak-like resin missing defect, and a spot resin missing defect the detected defect belongs to.

In the method of producing prepreg of the present invention, the optical device in the resin sheet inspection step preferably includes a light irradiation apparatus for irradiating the surface inspected for the defect with light, a light receiving apparatus for detecting reflected light from the surface of light emitted from the light irradiation apparatus, and a defect judgment apparatus for comparing an intensity value of the reflected light detected by the light receiving apparatus with a threshold value previously set to detect the defect and judging which of a streak-like resin missing defect, a foreign matter contamination defect and a spot resin missing defect the defect belongs to.

In the method of producing prepreg of the present invention, the optical device in the prepreg sheet inspection step preferably includes a light irradiation apparatus for irradiating the surface inspected for the defect with light, a light receiving apparatus for detecting reflected light from the surface of light emitted from the light irradiation apparatus, and a defect judgment apparatus for comparing an intensity value of the reflected light detected by the light receiving apparatus with a threshold value previously set to detect the defect and judging which of a carbon fiber fuzz defect, a foreign matter contamination defect, a carbon fiber bundle gap defect, a release paper wrinkle defect, a streak-like resin missing defect, and a spot resin missing defect the defect belongs to.

In the method of producing prepreg of the present invention, it is preferred that the defect judgment apparatus in the prepreg sheet inspection step previously sets a threshold value of at least one selected from the group consisting of brightness, width, length and area in each of signals of direct reflected light and signals of scattered reflected light for each of the carbon fiber fuzz defect, the foreign matter contamination defect, the carbon fiber bundle gap defect, the release paper wrinkle defect, the streak-like resin missing defect and the spot resin missing defect, determines the type of the reflected light to be used for detection based on the sensitivity of each reflected light for every defect, and classifies the detected defect into each defect by comparing these threshold values with the signals of the reflected light.

In the method of producing prepreg of the present invention, the defect judgment apparatus in the prepreg inspection step preferably classifies the defect into the carbon fiber fuzz defect, the carbon fiber bundle gap defect, the release paper wrinkle defect, the streak-like resin missing defect or the spot resin missing defect based on detected direct reflected light, and classifies the defect into the foreign matter contamination defect based on detected scattered reflected light.

In the method of producing prepreg of the present invention, it is preferred that the resin sheet supply step is provided on both sides of the carbon fiber sheet supplied by the carbon fiber sheet supply step with the carbon fiber sheet sandwiched between the resin sheet supply steps, and the detection of the defect in the surface of the prepreg sheet in the prepreg sheet inspection step is performed by the optical devices installed for both the surfaces of the prepreg sheet.

In the method of producing prepreg of the present invention, it is preferred that the resin sheet supply step is provided on both sides of the carbon fiber sheet supplied by the carbon fiber sheet supply step with the carbon fiber sheet sandwiched between the resin sheet supply steps, a plurality of the resin sheet supply steps are provided between the carbon fiber sheet supply step and the prepreg sheet taking-up step, and one of the release papers positioned at both outer surfaces of the prepreg sheet having passed through the resin impregnation step positioned at a position closest to the prepreg sheet taking-up step is separated, the prepreg sheet with the release paper, to which the other release paper adheres, is taken up by the prepreg sheet taking-up step, and the defect in the surface of the prepreg sheet, from which the one release paper has been separated, is inspected by the prepreg sheet inspection step.

In the method of producing prepreg of the present invention, the optical device in the prepreg sheet inspection step preferably includes a light irradiation apparatus for irradiating the surface inspected for the defect with light, a light receiving apparatus for detecting reflected light from the surface of light emitted from the light irradiation apparatus, and a defect judgment apparatus for comparing an intensity value of the reflected light detected by the light receiving apparatus with a threshold value previously set to detect the defect and judging which of a foreign matter contamination defect, a carbon fiber bundle gap defect, a release paper wrinkle defect, a streak-like resin missing defect, and a spot resin missing defect the defect belongs to, wherein the defect judgment apparatus classifies the defect into the foreign matter contamination defect, the carbon fiber bundle gap defect or the release paper wrinkle defect based on detected scattered reflected light, and classifies the defect into the streak-like resin missing defect or the spot resin missing defect based on detected direct reflected light.

In the method of producing prepreg of the present invention, it is preferred that the light irradiation apparatus in the prepreg sheet inspection step is a light irradiation apparatus of linear LED light, and the light receiving apparatus is a light receiving apparatus including a CCD line sensor camera.

In the method of producing prepreg of the present invention, it is preferred that the light irradiation apparatus in the resin sheet inspection step is a light irradiation apparatus employing a linear black light as a light source, and at least a pair of the black lights are placed so as to be symmetric with respect to a plane perpendicular to a running direction of the resin film and to be parallel to a straight line made by the plane and a resin film surface, and one or more black lights are placed for each of the ranges of incident angle of 40 to 80° and 100 to 140°.

In the method of producing prepreg of the present invention, it is preferred that the light receiving apparatus in the prepreg sheet inspection step is a light receiving apparatus including a CCD line sensor camera, and the CCD line sensor camera is installed at a camera installation angle of $\theta c$ in the range of −5 to +5° from a plane perpendicular to a running direction of the resin film.

In the method of producing prepreg of the present invention, the CCD line sensor camera is preferably provided with an optical filter for eliminating light in an ultraviolet region.

In the method of producing prepreg of the present invention, it is preferred that a position of the defect detected in the resin sheet inspection step or the prepreg sheet inspection step relative to the prepreg sheet is marked by a marking apparatus at a predetermined position at an end in a width direction of the release paper of the prepreg sheet taken up together with the release paper in the prepreg sheet taking-up step, and the type of the defect and the position of the defect in the prepreg sheet are determined by the marking.

A method of producing prepreg, including the above-mentioned steps in the method of producing prepreg and a prepreg sheet inspection step provided posterior to the prepreg sheet taking-up step among the above-mentioned steps, wherein the prepreg sheet inspection step has a defect information output step which transfers position information of the defect detected in the resin sheet inspection step or the prepreg sheet inspection step, or the position information and the type information of the defect to the prepreg sheet inspection step, identifies a position of the defect in the prepreg sheet inspection step by performing arithmetic computations using information on work in process in the prepreg sheet inspection step, and gives an alarm and/or decreases a moving speed of the prepreg sheet in the prepreg sheet inspection step when the defect appears in the prepreg sheet inspection step to enable confirmation of the defect, and outputs, as inspection results, defect information into which position information of the defect or position information and type information of the defect, and defect information and position information, respectively verified in the prepreg sheet inspection step, are consolidated.

In the method of producing prepreg having the inspection step, it is preferred to eliminate the defect area or attach a sign to the defect area according to treatment criteria of products previously set based on the confirmation of the defect.

The streak-like resin missing defect detected in the resin sheet inspection step or the prepreg sheet inspection step is a defect that a area where the resin is not coated or coating of the resin is incomplete, that is, a area where the resin is missed, appears in the shape of a streak in a longitudinal direction of the sheet in the inspection surface of the sheet.

The occurrence of the streak-like resin missing defect may result from the fact that in the preparation of the resin sheet, when the release paper is coated with resin by a coating roll, the resin is partially lost or continuously lost in a circumferential direction of the coating roll, and consequently the resin is missed in the shape of a streak on the release paper.

Further, the occurrence of the streak-like resin missing defect may result from the fact that a resin is missed in the shape of a streak at the surface of prepreg by defective transfer of the resin film which may occur when the resin film is transferred to the carbon fiber bundle by impregnating the resin film on the release paper into the carbon fiber bundle of the carbon fiber sheet in the resin impregnation step.

This streak-like resin missing defect may be briefly referred to as a streak defect.

The spot resin missing defect detected in the resin sheet inspection step or the prepreg sheet inspection step is a defect that a area where the resin is not coated or coating of the resin is incomplete, that is, a area where the resin is missed, appears in the shape of a point with varying area in an inspection surface of the sheet.

The occurrence of the spot resin missing defect may result from the fact that in the preparation of the resin sheet, when the release paper is coated with resin by a coating roll, the resin is partially lost on a circumferential surface of the coating roll, and consequently the resin is missed in the shape of a point on the release paper.

Further, the occurrence of the spot resin missing defect may result from the fact that a resin is missed in the shape of a point at the surface of prepreg by defective transfer of the resin film which may occur when the resin film is transferred to the carbon fiber bundle by impregnating the resin film on the release paper into the carbon fiber bundle of the carbon fiber sheet in the resin impregnation step.

This spot resin missing defect may be briefly referred to as a resin missing defect.

The foreign matter contamination defect detected in the resin sheet inspection step or the prepreg sheet inspection step is a defect that appears by the mixing of foreign matters of various sizes into a resin in an inspection surface of the sheet.

The occurrence of the foreign matter contamination defect may result from the mixing of foreign matters adhered to the apparatus used in preparation of the resin sheet, such as lumps of cured resin having various sizes or fragments of a release paper, into the resin film.

Further, the occurrence of the foreign matter contamination defect may result from the mixing of foreign matters adhered to the apparatus used in the carbon fiber sheet supply step, the laminated sheet forming step or the resin impregnation step, such as lumps of carbon fibers having various sizes, lumps of cured resin having various sizes or fragments of a release paper, into the prepreg.

This foreign matter contamination defect may be briefly referred to as a foreign matter defect.

The carbon fiber fuzz defect detected in the prepreg sheet inspection step is a defect that appears by the mixing of fuzz of the carbon fiber derived from the carbon fiber bundle into prepreg or by the adhesion of the fuzz to prepreg.

This carbon fiber fuzz defect may be briefly referred to as a fuzz defect.

The carbon fiber bundle gap defect detected in the prepreg sheet inspection step is a defect that appears due to a gap which exists in the carbon fiber bundle to be supplied to the carbon fiber sheet supply step, the carbon fiber bundle in the carbon fiber sheet running from the carbon fiber sheet supply step to the resin impregnation step through the laminated sheet forming step or the carbon fiber bundle in the resin impregnation step, or a gap which is produced in these processes and appears between a lot of arranged carbon fibers or a plurality of arranged carbon fiber bundles, where the carbon fiber is not present.

This carbon fiber bundle gap defect may be briefly referred to as a gap defect.

A wrinkle may occur in the release paper when the release paper passes through the resin sheet supply step, the laminated sheet forming step or the resin impregnation step. The release paper wrinkle defect detected in the prepreg sheet inspection step is a defect that appears at the surface of prepreg by transfer of the wrinkle of the release paper to the prepreg.

This release paper wrinkle defect may be briefly referred to as a wrinkle defect.

These defects respectively have a peculiar shape. Thus, it is previously performed to visually observe each peculiar shape to identify what kinds of defects are produced in the production process of the prepreg. Further, as shown in Patent Documents 1 to 5, it is previously performed to detect each peculiar shape by an optical device to identify what kinds of defects are produced in the production process of the prepreg.

Judgment of each defect in the resin sheet inspection step and judgment of each defect in the prepreg sheet inspection step are made by using the peculiar shape of each defect.

That is, a sample having a defect serving as an inspection object is prepared, the defect is detected by the optical device by using the sample, and values of brightness, width, length and area of the defect are acquired. On the other hand, a threshold value of the brightness is determined based on information on the kind of prepreg to be produced such as the type of a release paper to be used, the type of a resin and the weight per a unit area of a resin film formed on the release paper. Further, threshold values for the width, the length and the area of the defect are determined according to characteristics required of the intended prepreg.

By comparing data on the defects which is detected and acquired by the optical device in the resin sheet inspection step or the prepreg sheet inspection step with the threshold values determined, the type of the defect is judged. Further, data on the position of the defect is acquired.

The reflected light from the inspection surface of light emitted from the light irradiation apparatus equipped in the optical device is received by the light receiving apparatus equipped in the optical device, and the detection of the defect is performed based on signals related to the received light. As the reflected light, direct reflected light and scattered reflected light can be used. It is preferred that the direct reflected light is used for detection of the streak defect, the resin missing defect and the fuzz defect, either of the direct reflected light and the scattered reflected light is used for detection of the gap defect and the wrinkle defect, and the scattered reflected light is used for detection of the foreign matter defect.

According to the present invention, in producing prepreg, since the defect in the surface of the resin film formed by coating the release paper with a resin to be impregnated into the carbon fiber bundle is detected at a position prior to the laminated sheet forming step in which the carbon fiber sheet and the resin sheet are laminated, the defect of the prepreg sheet which is formed in the resin impregnation step after the laminated sheet forming step can be identified with reliability.

Further, according to the present invention, when the method of producing prepreg includes at least two resin impregnation steps of impregnating a resin into a carbon fiber bundle, it becomes possible to detect the defect of both surfaces of the prepreg to which a release paper is not adhered. Moreover, according to the present invention, since quality of the prepreg ultimately produced after finishing the inspection step can be identified by judging the detected defect based on a criterion according to the type of the defect, and transferring the result of the judgment to the inspection step, not only the inspection time can be shortened, but also the quality of the prepreg product can be outstandingly improved.

DETAILED DESCRIPTION OF EMBODIMENTS OF THE INVENTION

Figure 1:
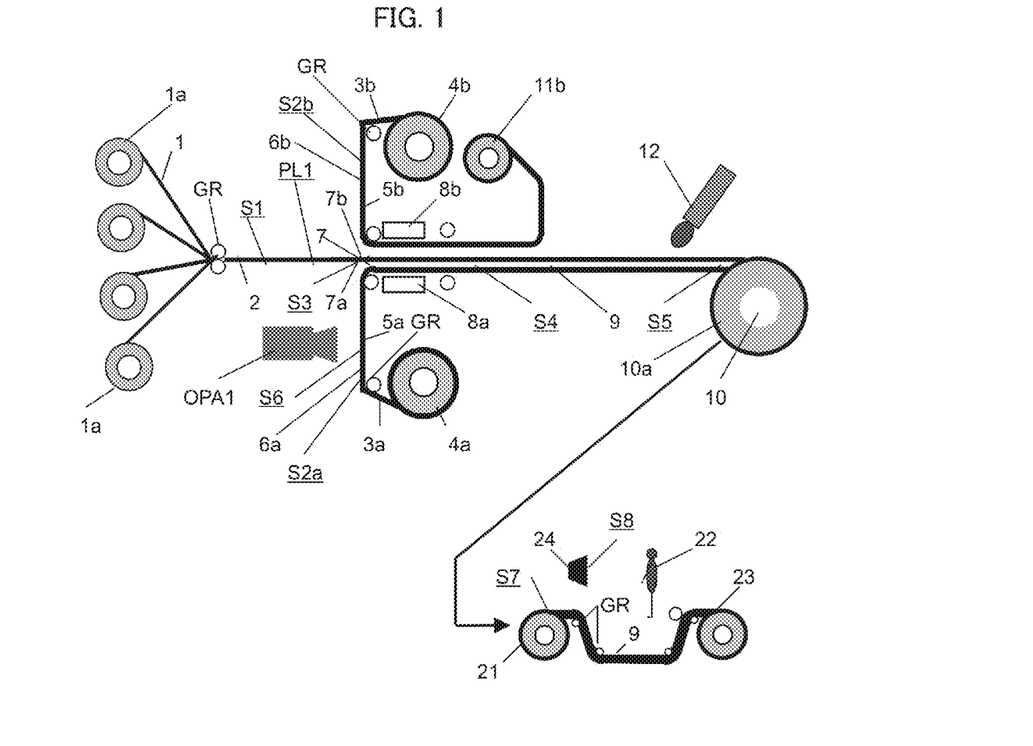
FIG. 1 is a schematic side view of an example of an apparatus for producing prepreg for implementing a method of producing prepreg of the present invention.

A first embodiment of the method of producing prepreg of the present invention will be described with reference to the apparatus for producing prepreg shown in FIG. 1. FIG. 1 is a schematic side view of an example of an apparatus for producing prepreg for implementing a method of producing prepreg of the present invention.

The apparatus for producing prepreg shown in FIG. 1 has a carbon fiber sheet supply step S1 on a left side. Bobbins 1a, around which a carbon fiber bundle 1 is wound, are rotatably mounted on a creel (not shown) at a left end of the carbon fiber sheet supply step S1. Usually, the creel is provided with a lot of bobbins 1a placed at intervals in a vertical direction in FIG. 1 and in a direction parallel to the plane of paper of FIG. 1. In FIG. 1, four bobbins 1a in one vertical row are illustrated.

In the production of prepreg, each carbon fiber bundle 1 continuously wound off from each bobbin 1a passes between guide rolls GR each positioned at intervals in a vertical direction and reaches a prepreg sheet production line PL1. Each carbon fiber bundle 1 reaching the prepreg sheet production line PL1 is arranged in directions of width and thickness in agreement with the width and thickness of the prepreg sheet to be produced to form a carbon fiber sheet 2.

Resin sheet supply steps S2a and S2b are provided downstream of the carbon fiber sheet supply step S1 along the prepreg sheet production line PL1. The resin sheet supply steps S2a and S2b are positioned on vertically opposite sides of the prepreg sheet production line PL1.

In the resin sheet supply step S2a, a resin sheet roll 4a, around which a resin sheet 3a is rolled up, is provided and rotatably attached to a roll axis (not shown). The resin sheet 3a includes a release paper 5a and a resin film 6a formed by coating the surface of the release paper 5a with a resin.

In the production of prepreg, the resin sheet 3a continuously wound off from the resin sheet roll 4a passes between the guide rolls GR and reaches the prepreg sheet production line PL1. In FIG. 1, two guide rolls GR are illustrated in the resin sheet supply step S2a. When the resin sheet 3a passes between the guide rolls GR, an outer surface (surface on a side where the resin film 6a is not coated) of the release paper 5a of the resin sheet 3a is brought into contact with the periphery of the guide rolls GR and passes between the guide rolls GR.

In the resin sheet supply step S2b, a resin sheet roll 4b, around which a resin sheet 3b is rolled up, is provided and rotatably attached to a roll axis (not shown). The resin sheet 3b includes a release paper 5b and a resin film 6b formed by coating the surface of the release paper 5b with a resin. In the production of prepreg, the resin sheet 3b continuously wound off from the resin sheet roll 4b passes between the guide rolls GR and reaches the prepreg sheet production line PL1. In FIG. 1, two guide rolls GR are illustrated in the resin sheet supply step S2b. When the resin sheet 3b passes between the guide rolls GR, an outer surface (surface on a side where the resin film 6b is not coated) of the release paper 5b of the resin sheet 3b is brought into contact with the periphery of the guide rolls GR and passes between the guide rolls GR.

The apparatus for producing prepreg shown in FIG. 1 has two resin sheet supply steps S2a and S2b, but the upper resin sheet supply step S2b of these resin supply steps may be omitted depending on a prepreg sheet to be produced.

A laminated sheet forming step S3 is provided downstream of the carbon fiber sheet supply step S1 and the resin sheet supply steps S2a and S2b. In the laminated sheet forming step S3, the surface of the resin film 6a of the resin sheet 3a supplied from the resin sheet supply step S2a is opposed to a lower surface of the carbon fiber sheet 2 supplied from the carbon fiber sheet supply step S1, and a laminated sheet 7a including the carbon fiber sheet 2 and the resin sheet 3a is formed.

Further, in the laminated sheet forming step S3, the surface of the resin film 6b of the resin sheet 3b supplied from the resin sheet supply step S2b is opposed to an upper surface of the carbon fiber sheet 2 supplied from the carbon fiber sheet supply step S1, and a laminated sheet 7b including the carbon fiber sheet 2 and the resin sheet 3b is formed. Thereby, a laminated sheet 7 combining the laminated sheet 7a and the laminated sheet 7b is formed.

A resin impregnation step S4 is provided downstream of the laminated sheet forming step S3 along the prepreg sheet production line PL1. In the resin impregnation step S4, a heater 8a is placed below the prepreg sheet production line PL1. A heater 8b opposed to the lower heater 8a is placed at an interval on the upper side of the prepreg sheet production line PL1.

The laminated sheet 7 formed in the laminated sheet forming step S3 is heated during passage between the heater 8a and the heater 8b, and thereby, the resin composing the resin films 6a and 6b is impregnated into the carbon fiber bundle 1. A prepreg sheet 9 is formed by impregnation of the resin into the carbon fiber bundle.

In impregnating the resin into the carbon fiber bundle 1, there may be cases where it is better to apply a pressure. In that case, usually, a rotatable pressure nip roll (not shown) is used. In addition, there is a system in which movement of the laminated sheet 7 is stopped once and the laminated sheet 7 is sandwiched between the heater 8a and the heater 8b and pressurized, but this system is not preferable since the movement of the laminated sheet 7 is intermittent.

A prepreg sheet taking-up step S5 is provided downstream of the resin impregnation step S4 along the prepreg sheet production line PL1. In the prepreg sheet taking-up step S5, a prepreg sheet taking-up apparatus 10 is placed. The prepreg sheet 9 formed in the resin impregnation step S4 is taken up by the prepreg sheet taking-up apparatus 10 to form a prepreg sheet roll 10a.

In a process of movement of the prepreg sheet 9 from the resin impregnation step S4 to the prepreg sheet taking-up step S5, the release paper 5b of the resin sheet 3b is separated from the prepreg sheet 9, and taken up by a release paper taking up apparatus 11b. The prepreg sheet 9 without the release paper 5b, moving toward the prepreg sheet taking-up apparatus 10, is a prepreg sheet having the release paper 5a adhered to the lower surface thereof. That is, the prepreg sheet 9 taken up by the prepreg sheet taking-up apparatus 10 is a prepreg sheet with a release paper in which a release paper adheres to one surface of the prepreg sheet.

The apparatus for producing prepreg shown in FIG. 1 has a resin sheet inspection step S6 in the resin sheet supply step S2a. In the resin sheet inspection step S6, an optical device OPA1 for detecting the defect in the surface of the resin film 6a of the resin sheet 3a is provided. The optical device OPA1 detects the defect present at the surface of the resin film 6a, and judges which of a streak-like resin missing defect, a foreign matter contamination defect and a spot resin missing defect the detected defect belongs to.

In the resin sheet supply step S2b, a resin sheet inspection step may be provided and a similar optical device may be installed for the same purpose.

The apparatus for producing prepreg shown in FIG. 1 has a marking apparatus 12 for marking the type of the defect and the position of the defect in the prepreg sheet, which are obtained from the judgment of the defect detected in the resin sheet inspection step S6, at a predetermined position at an end in a width direction of the release paper 5a of the prepreg sheet 9. Thereby, the type and the position of the defect are marked on the release paper 5a of the prepreg sheet 9.

The apparatus for producing prepreg shown in FIG. 1 has a prepreg sheet inspection step S7 of detaching the prepreg sheet roll 10a formed in the prepreg sheet taking-up apparatus 10 from the prepreg sheet taking-up apparatus 10, and inspecting the roll 10a.

The prepreg sheet inspection step S7 has a winding-off apparatus 21 for attaching the prepreg sheet roll 10a transferred from the prepreg sheet taking-up apparatus 10, a guide roll GR for moving the prepreg sheet 9 unwound from the winding-off apparatus 21 arranged for visual inspection of the prepreg sheet 9 by a inspector 22, and a taking-up apparatus 23 for taking up the prepreg sheet 9 after completion of inspection.

Further, the prepreg sheet inspection step S7 has a defect information output step S8 for transferring information on the defect of the prepreg sheet 9 to the inspector 22 by means of sound or light. The defect information output step S8 is provided with an alarm device 24 for transferring information on the defect of the prepreg sheet 9 to the inspector 22 by means of sound or light.

The first embodiment of the method of producing prepreg of the present invention described with reference to the apparatus for producing prepreg shown in FIG. 1 has the greatest feature in that in the resin sheet inspection step S2a, the defect in the surface of the resin film 6a of the resin sheet 3a before moving toward the laminated sheet forming step S3 is detected by the optical device OPA1, and the optical device OPA1 judges which type of defect the detected defect belongs to. Thereby, the defect in the surface of the resin film 6a on the side opposite to the release paper 5a, where the release paper is not present, can be detected, and the type of the defect can be identified. This defect will appear, if present, as a defect of a prepreg sheet subsequently formed.

Figure 2:
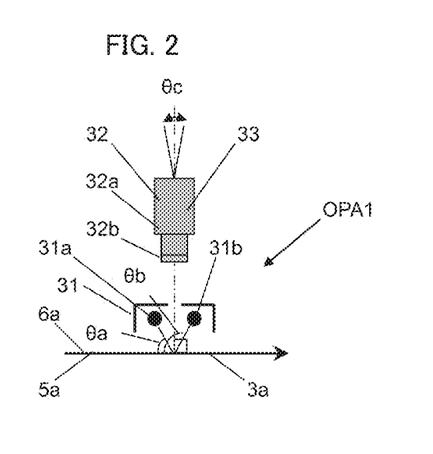
FIG. 2 is a schematic side sectional view of an example of an optical device used for detection of a defect in the apparatus for producing prepreg shown in FIG. 1.

FIG. 2 is a schematic side sectional view of an example of the optical device OPA1 used for detection of a defect of the resin film 6a in the resin sheet inspection step S6 in the apparatus for producing prepreg shown in FIG. 1.

In FIG. 2, the optical device OPA1 includes a light irradiation apparatus 31 for irradiating the surface of the resin film 6a with light, a light receiving apparatus 32 for detecting reflected light from the surface of the resin film 6a of light emitted from the light irradiation apparatus 31, and a defect judgment apparatus 33 for comparing an intensity value of the reflected light detected by the light receiving apparatus 32 with a threshold value previously set and judging which of a streak-like resin missing defect, a foreign matter contamination defect and a spot resin missing defect the defect in the surface of the resin film 6a belongs to.

The light irradiation apparatus 31 has light sources 31a and 31b. These light sources 31a and 31b are not particularly limited as long as they emit ultraviolet light. These light sources 31a and 31b are preferably linear black lights. The number of the light sources may be one. However, the light source preferably includes at least a pair of lights so as to be perpendicular to the surface of the resin film 6a and to be symmetric with respect to a plane perpendicular to a running direction of the resin film 6a, and is preferably placed so as to irradiate the whole width of the resin film 6a. In this case, it is preferred that the light source 31a is placed in such a way that an incident angle $\theta a$ falls within a range of 40 to 80°, and the light source 31b is placed in such a way that an incident angle $\theta b$ falls within a range of 100 to 140°.

Since the incident angle $\theta a$ is 40° or more relative to the surface of the resin film 6a, light quantity of the reflected light can be held even when the light source output is low. Further, the closer the incident angle $\theta a$ to 90°, the more the reflected light is intensified, but the incident angle $\theta a$ is preferably 80° or less in terms of machine installation.

Similarly, since incident angle $\theta b$ is 140° or less relative to the surface of the resin film 6a, light quantity of the reflected light can be held even when the light source output is low. Further, the closer the incident angle $\theta b$ to 90°, the more the reflected light is intensified, but the incident angle $\theta b$ is preferably 100° or more in terms of machine installation.

The reflected light means at least one light of reflected light itself of light emitted from the light source to the surface of the resin film 6a, and light which is newly excited and emitted by irradiation light.

The defect judgment apparatus 33 preferably includes a signal processing means in which threshold values of brightness, width, length, area and the like are previously set by types of the prepreg sheet products to be produced, and a means for computing signals in a scanning direction of the light receiving apparatus 32 to a direction of a temporal axis, and judging the presence or absence of a defect, and the type, position and level of the defect.

The light receiving apparatus 32 includes a camera 32a which is opposed to the surface of the resin film 6a moving in the right direction of FIG. 2 at a predetermined speed. The reflected light from the surface of the resin film 6a is detected by the camera 32a. The camera 32a is not particularly limited as long as it is a camera including a sensor capable of generating signals according to the level of the detected reflected light.

As a typical camera, a CCD line sensor camera can be used. The camera 32a is preferably placed at a camera installation angle of θc in the range of −5 to +5° from a plane perpendicular to a running direction of the resin film 6a.

In general, light in an ultraviolet region is easily absorbed in a resin, particularly an epoxy resin which is often used as a resin for prepreg and has a curing temperature of 130° C. or 180° C., and it is known that excited luminescence having a longer wavelength than ultraviolet light occurs by absorption of the ultraviolet light.

When the resin film 6a formed by coating the release paper with a resin is irradiated with ultraviolet rays, and light quantity of reflected light is observed, quantity of the excited luminescence is decreased in the defect area where coating is defective and/or foreign matters adhere compared with an area of normal coating. By using this phenomenon, since there is a difference in the quantity of the excited luminescence between the area of normal coating and the area of defective coating, it becomes possible to discriminate the normal area from the defective area of the resin film 6a by observing the quantity of the excited luminescence and detecting an output difference between both the areas.

In order to emphasize the reflected light based on excited luminescence of the reflected light from the surface of the resin film 6a, it is preferred to provide an optical filter 32b. The optical filter 32b is preferably a filter that cuts off light having a wavelength of 300 to 400 nm in order to cut off an ultraviolet wavelength.

For example, it is preferred that the threshold values are ultimately determined by first reading a sample of a defect serving as a reference in an inspection apparatus, setting threshold values based on values of brightness, width, length, area and the like for the sample, and then adjusting the threshold values in the actual steps. Specifically, first, a threshold value of the brightness is determined from information peculiar to that kind such as the type of a release paper, the type of a resin and the weight per unit area of a resin. Next, a streak-like resin missing defect is distinguished from other defects by using the information of width and length, and a foreign matter contamination defect and a spot resin missing defect are distinguished from other defects by using the area information, and thereby threshold values may be determined.

Figure 3:
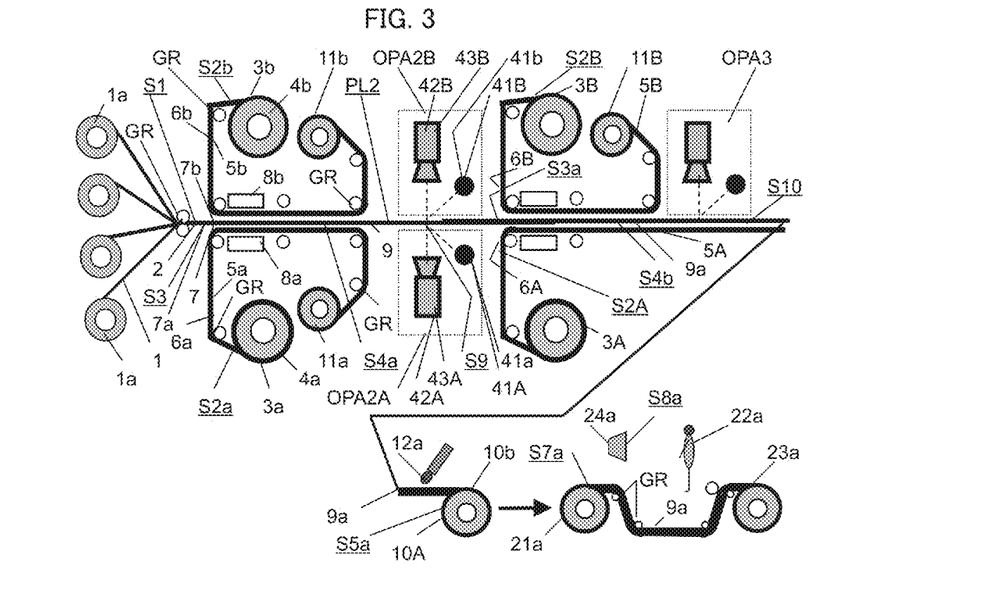
FIG. 3 is a schematic side view of another example of an apparatus for producing prepreg for implementing a method of producing prepreg of the present invention.

A second embodiment of the method of producing prepreg of the present invention will be described with reference to the apparatus for producing prepreg shown in FIG. 3. FIG. 3 is a schematic side view of an example of an apparatus for producing prepreg for implementing the method of producing prepreg of the present invention. The apparatus for producing prepreg shown in FIG. 3 has two resin impregnation steps of a first resin impregnation step and a second resin impregnation step at an interval in a direction of movement of the prepreg sheet along a prepreg sheet production line PL2. Further, the release paper on at least one surface of the prepreg sheet is separated when the prepreg sheet has passed through the first resin impregnation step, and the defect in the surface of the prepreg sheet where the release paper is not present is detected. The apparatus for producing prepreg shown in FIG. 3 is, at least in these points, different from the apparatus for producing prepreg shown in FIG. 1, in which the number of the resin impregnation steps is one and the defect of the surface of the resin film moving toward the resin impregnation step is detected.

The apparatus for producing prepreg shown in FIG. 3 has a carbon fiber sheet supply step S1 on a left side. Bobbins 1a, around which a carbon fiber bundle 1 is wound, are rotatably mounted on a creel (not shown) at a left end of the carbon fiber sheet supply step S1. Usually, the creel is provided with a lot of bobbins 1a placed at intervals in a vertical direction in FIG. 3 and in a direction parallel to the plane of paper of FIG. 3. In FIG. 3, four bobbins 1a in one vertical row are illustrated.

In the production of prepreg, each carbon fiber bundle 1 continuously wound off from each bobbin 1a passes between guide rolls GR each positioned at intervals in a vertical direction and reaches a prepreg sheet production line PL2. Each carbon fiber bundle 1 reaching the prepreg sheet production line PL2 is arranged in directions of width and thickness in agreement with the width and thickness of the prepreg sheet to be produced to form a carbon fiber sheet 2.

Resin sheet supply steps S2a and S2b are provided downstream of the carbon fiber sheet supply step S1 along the prepreg sheet production line PL2. The resin sheet supply steps S2a and S2b are positioned on vertically opposite sides of the prepreg sheet production line PL2.

In the resin sheet supply step S2a, a resin sheet roll 4a, around which a resin sheet 3a is rolled up, is provided and rotatably attached to a roll axis (not shown). The resin sheet 3a includes a release paper 5a and a resin film 6a formed by coating the surface of the release paper 5a with a resin.

In the production of prepreg, the resin sheet 3a continuously wound off from the resin sheet roll 4a passes between the guide rolls GR and reaches the prepreg sheet production line PL2. In FIG. 3, two guide rolls GR are illustrated in the resin sheet supply step S2a. When the resin sheet 3a passes between the guide rolls GR, an outer surface (surface on a side where the resin film 6a is not coated) of the release paper 5a of the resin sheet 3a is brought into contact with the periphery of the guide rolls GR and passes between the guide rolls GR.

In the resin sheet supply step S2b, a resin sheet roll 4b, around which a resin sheet 3b is rolled up, is provided and rotatably attached to a roll axis (not shown). The resin sheet 3b includes a release paper 5b and a resin film 6b formed by coating the surface of the release paper 5b with a resin. In the production of prepreg, the resin sheet 3b continuously wound off from the resin sheet roll 4b passes between the guide rolls GR and reaches the prepreg sheet production line PL2. In FIG. 3, two guide rolls GR are illustrated in the resin sheet supply step S2b. When the resin sheet 3b passes between the guide rolls GR, an outer surface (surface on a side where the resin film 6b is not coated) of the release paper 5b of the resin sheet 3b is brought into contact with the periphery of the guide rolls GR and passes between the guide rolls GR.

The apparatus for producing prepreg shown in FIG. 3 has two resin sheet supply steps S2a and S2b, but one resin sheet supply step of these resin sheet supply steps may be omitted depending on a prepreg sheet to be produced.

A laminated sheet forming step S3 is provided downstream of the carbon fiber sheet supply step S1 and the resin sheet supply steps S2a and S2b. In the laminated sheet forming step S3, the surface of the resin film 6a of the resin sheet 3a supplied from the resin sheet supply step S2a is opposed to a lower surface of the carbon fiber sheet 2 supplied from the carbon fiber sheet supply step S1, and a laminated sheet 7a including the carbon fiber sheet 2 and the resin sheet 3a is formed.

Further, in the laminated sheet forming step S3, the surface of the resin film 6*b* of the resin sheet 3*b* supplied from the resin sheet supply step S2*b* is opposed to an upper surface of the carbon fiber sheet 2 supplied from the carbon fiber sheet supply step S1, and a laminated sheet 7*b* including the carbon fiber sheet 2 and the resin sheet 3*b* is formed. Thereby, a laminated sheet 7 combining the laminated sheet 7*a* and the laminated sheet 7*b* is formed.

A first resin impregnation step S4*a* is provided downstream of the laminated sheet forming step S3 along the prepreg sheet production line PL2. In the first resin impregnation step S4*a*, a heater 8*a* is placed below the prepreg sheet production line PL2. A heater 8*b* opposed to the lower heater 8*a* is placed at an interval on the upper side of the prepreg sheet production line PL2.

The laminated sheet 7 formed in the laminated sheet forming step S3 is heated during passage between the heater 8*a* and the heater 8*b*, and thereby, the resin composing the resin films 6*a* and 6*b* is impregnated into the carbon fiber bundle 1. A prepreg sheet 9 is formed by impregnation of the resin into the carbon fiber bundle.

In impregnating the resin into the carbon fiber bundle 1, there may be cases where it is better to apply a pressure. In that case, usually, a rotatable pressure nip roll (not shown) is used. In addition, there is a system in which movement of the laminated sheet 7 is stopped once and the laminated sheet is sandwiched between the heater 8*a* and the heater 8*b* and pressurized, but this system is not preferable since the movement of the laminated sheet 7 is intermittent.

In a process of movement of the prepreg sheet 9 formed in the first resin impregnation step S4*a* to the downstream side along the prepreg sheet production line PL2, the release paper 5*a* supporting the resin film 6*a* is separated from the resin film 6*a*, moves along five guide rolls GR, and is taken up by a release paper taking up apparatus 11*a*. Further, the release paper 5*b* supporting the resin film 6*b* is separated from the resin film 6*b*, moves along five guide rolls GR, and is taken up by a release paper taking up apparatus 11*b*.

The prepreg sheet 9, from which the release paper has been removed, moves downstream along the prepreg sheet production line PL2 and reaches a prepreg sheet inspection step S9. In the prepreg sheet inspection step S9, an optical device OPA2A for detecting the defect in the surface of the prepreg sheet 9 is provided below the prepreg sheet production line PL2. Further, in the prepreg sheet inspection step S9, an optical device OPA2B for detecting the defect in the surface of the prepreg sheet 9 is provided above the prepreg sheet production line PL2.

The optical devices OPA2A and OPA2B detect the defect present at the surface of the prepreg sheet 9, and judge which of a carbon fiber fuzz defect, a foreign matter contamination defect, a carbon fiber bundle gap defect, a release paper wrinkle defect, a streak-like resin missing defect, and a spot resin missing defect the detected defect belongs to.

The optical device OPA2A includes a light irradiation apparatus 41A for irradiating the surface of the prepreg sheet 9 with light, a light receiving apparatus 42A for detecting reflected light from the surface of the prepreg sheet 9 of light emitted from the light irradiation apparatus 41A, and a defect judgment apparatus 43A for comparing an intensity value of the reflected light detected by the light receiving apparatus 42A with a threshold value previously set to detect the defect in the surface of the prepreg sheet 9 and judging which of a carbon fiber fuzz defect, a foreign matter contamination defect, a carbon fiber bundle gap defect, a release paper wrinkle defect, a streak-like resin missing defect, and a spot resin missing defect the detected defect belongs to.

The optical device OPA2B, as with the optical device OPA2A, includes a light irradiation apparatus 41B for irradiating the surface of the prepreg sheet 9 with light, a light receiving apparatus 42B for detecting reflected light from the surface of the prepreg sheet 9 of light emitted from the light irradiation apparatus 41B, and a defect judgment apparatus 43B for comparing an intensity value of the reflected light detected by the light receiving apparatus 42B with a threshold value previously set to detect the defect in the surface of the prepreg sheet 9 and judging which of a carbon fiber fuzz defect, a foreign matter contamination defect, a carbon fiber bundle gap defect, a release paper wrinkle defect, a streak-like resin missing defect, and a spot resin missing defect the detected defect belongs to.

The light irradiation apparatus 41A has a light source 41*a*, and the light irradiation apparatus 41B has a light source 41*b*. These light sources 41*a* and 41*b* are not particularly limited as long as a light-emitting part has a shape which extends linearly in a width direction of the prepreg sheet 9. As the light sources 41*a* and 41*b*, linear LED lights are preferably used.

The light receiving apparatuses 42A and 42B are not particularly limited as long as they are apparatuses including sensors capable of detecting the reflected light from the surface of the prepreg sheet 9 and generating signals according to the level of the detected reflected light. As the light receiving apparatuses 42A and 42B, a CCD line sensor camera is preferably used.

In general, it is known that the reflected light is classified into scattered reflected light and direct reflected light, and the defect can be clearly detected by selectively using these reflected lights according to the defect type. Further, as described in Patent Documents 1 and 2, the reflected light can be separated into a light signal and a dark signal depending on the defect. The defect can be more clearly detected by discriminating the light signal from the dark signal.

It is preferred that, specifically, the defect judgment apparatus previously discriminates a light reaction from a dark reaction, sets a threshold value of at least any one selected from the group consisting of brightness, width, length and area in each of signals of direct reflected light and signals of scattered reflected light for each of the carbon fiber fuzz defect, the foreign matter contamination defect, the carbon fiber bundle gap defect, the release paper wrinkle defect, the streak-like resin missing defect and the spot resin missing defect, determines the type of the reflected light to be used for detection based on the sensitivity of each reflected light for every defect, and classifies the detected defect into each defect by comparing these threshold values with the signals of the reflected light.

As described above, various kinds of defects are classified into defects judged by the direct reflected light and defects judged by the scattered reflected light, and classified into defects appearing as a light signal and defects appearing as a dark signal when appropriate threshold values are determined, and classification of the defect becomes possible by concurrent use of two-dimensional shape information or some other information. For example, when the defect in the surface of the prepreg sheet 9 is inspected, the carbon fiber fuzz defect, the carbon fiber bundle gap defect, the release paper wrinkle defect, the streak-like resin missing defect and the spot resin missing defect can be identified by receiving the direct reflected light from the surface of the prepreg sheet 9 by the light receiving apparatus, and the foreign matter contamination defect can be identified by receiving the scattered reflected light from the surface of the prepreg sheet 9 by the light receiving apparatus.

When the direct reflected light and the scattered reflected light are used, two or more light sources and two or more light receiving apparatuses are placed at each inspection position, but it is more preferable that two light sources and one light receiving apparatus are placed at each inspection position in order to downsize the inspection apparatus.

Further, an angle of irradiation with light emitted from the light source to the surface of prepreg is preferably 30 to 85° relative to the surface of prepreg when the direct reflected light is used, and is preferably 5 to 60° relative to the surface of prepreg when the scattered reflected light is used. When the direct reflected light is used for emphasizing each reflected light, the angle of irradiation with light is more preferably 40 to 80° relative to the surface of prepreg, and when the scattered reflected light is used, the angle of irradiation with light is more preferably 10 to 50° relative to the surface of prepreg.

Moreover, in the case of direct reflected light, the light receiving angle of the light receiving apparatus is preferably 0° or more in a direction opposite to an incident direction of light from the right source from a plane perpendicular to a running direction of the prepreg, and the light receiving angle is more preferably 0 to 60° for detecting both of the direct reflected light and the scattered reflected light with two light sources and one light receiving apparatus.

The prepreg sheet 9 having passed through the prepreg sheet inspection step S9 moves to a second resin impregnation step S4b. A resin sheet supply step S2A for supplying the resin sheet 3A to a lower surface side of the prepreg sheet 9 and a resin sheet supply step S2B for supplying the resin sheet 3B to an upper surface side of the prepreg sheet 9 are provided between the prepreg sheet inspection step S9 and the second resin impregnation step S4b.

The resin sheet supply step S2A is a step similar to the resin sheet supply step S2a shown in FIG. 1. Further, the resin sheet supply step S2B is a step similar to the resin sheet supply step S2b shown in FIG. 1. The resin sheet 3A supplied from the resin sheet supply step S2A, the resin sheet 3B supplied from the resin sheet supply step S213, and the prepreg sheet 9 are laminated in a laminated sheet forming step Sia, and then moved to a second resin impregnation step S4b. The second resin impregnation step S4b is a step similar to the resin impregnation step S4 shown in FIG. 1.

In the second resin impregnation step S4b, a resin film 6A of the resin sheet 3A and a resin film 6B of the resin sheet 3B are impregnated into the prepreg sheet 9 to form a second prepreg sheet 9a.

A prepreg sheet taking-up step S5a is provided downstream of the second resin impregnation step S4b along the prepreg sheet production line PL2. In the prepreg sheet taking-up step S5a, a prepreg sheet taking-up apparatus 10A is placed. The second prepreg sheet 9a formed in the second resin impregnation step S4b is taken up by the prepreg sheet taking-up apparatus 10A to form a prepreg sheet roll 10b.

In a process of movement of the second prepreg sheet 9a from the second resin impregnation step S4b to the prepreg sheet taking-up step S5a, the release paper 5B of the resin sheet 3B is separated from the prepreg sheet 9a, and taken up by a release paper taking up apparatus 11B. The prepreg sheet 9a without the release paper 5B, moving toward the prepreg sheet taking-up apparatus 10A, is a prepreg sheet having a release paper 5A adhered to the lower surface thereof. That is, the prepreg sheet 9a taken up by the prepreg sheet taking-up apparatus 10A is a prepreg sheet with a release paper in which a release paper adheres to one surface of the prepreg sheet.

The apparatus for producing prepreg shown in FIG. 3 has a prepreg sheet inspection step S10 for inspecting the defect in the surface of the prepreg sheet 9a from which the release paper has been separated, which moves toward the prepreg sheet taking-up apparatus 10A. In the prepreg sheet inspection step S10 is installed an optical device OPA3 for detecting the defect in the surface of the prepreg sheet 9a from which the release paper has been separated. The optical device OPA3 is an apparatus similar to the optical device OPA2A. The presence or absence and the type of the defect in the surface of the prepreg sheet 9a before being taken up by the prepreg sheet taking-up apparatus 10A are judged by the optical device OPA3.

The apparatus for producing prepreg shown in FIG. 3 has a marking apparatus 12a for marking the type of the defect and the position of the defect in the prepreg sheet, which are obtained from the judgment of the defects detected in the prepreg sheet inspection steps S9 and S10, at a predetermined position at an end in a width direction of the release paper 5A of the prepreg sheet 9a. Thereby, the type and the position of the defect are marked on the release paper 5A of the prepreg sheet 9a.

The apparatus for producing prepreg shown in FIG. 3 has a prepreg sheet inspection step S7a of detaching the prepreg sheet roll 10b formed in the prepreg sheet taking-up apparatus 10A from the prepreg sheet taking-up apparatus 10A, and inspecting the roll 10b.

The prepreg sheet inspection step S7a has a winding-off apparatus 21a for attaching the prepreg sheet roll 10b transferred from the prepreg sheet taking-up apparatus 10A, a guide roll GR for moving the prepreg sheet 9a unwound from the winding-off apparatus 21a arranged for visual inspection of the prepreg sheet 9a by an inspector 22a, and a taking-up apparatus 23a for taking up the prepreg sheet 9a after completion of inspection.

Further, the prepreg sheet inspection step S7a has a defect information output step S8a for transferring information on the defect of the prepreg sheet 9a to the inspector 22a by means of sound or light. The defect information output step S8a is provided with an alarm device 24a for transferring information on the defect of the prepreg sheet 9a to the inspector 22a by means of sound or light.

The second embodiment of the method of producing prepreg of the present invention described with reference to the apparatus for producing prepreg shown in FIG. 3 has the greatest feature in that in the prepreg sheet inspection step S9, the inspection of the defect is performed on both surfaces of the prepreg sheet where the release paper is not present. Further, in the prepreg sheet inspection step S10, inspection of the defect is performed at the surface of the prepreg sheet moving toward the taking-up apparatus, where the release paper is not present.

Figure 4:
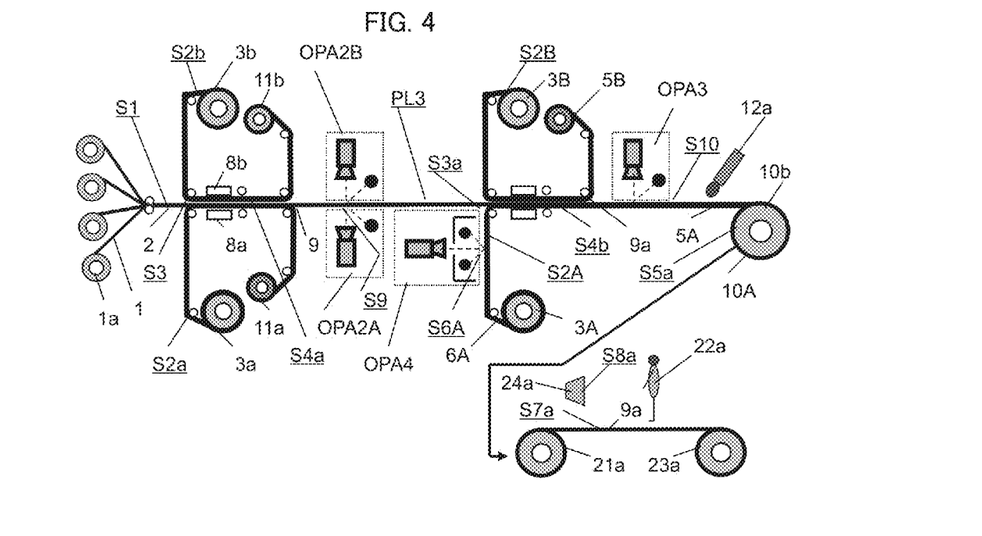
FIG. 4 is a schematic side view of still another example of an apparatus for producing prepreg for implementing a method of producing prepreg of the present invention.

A third embodiment of the method of producing prepreg of the present invention will be described with reference to the apparatus for producing prepreg shown in FIG. 4. FIG. 4 is a schematic side view of an example of an apparatus for producing prepreg for implementing the method of producing prepreg of the present invention. The apparatus for producing prepreg shown in FIG. 4 has two resin impregnation steps of a first resin impregnation step and a second resin impregnation step at an interval in a direction of movement of the prepreg sheet along a prepreg sheet production line PL3. Further, the release paper on at least one surface of the prepreg sheet is separated when the prepreg sheet has passed through the first resin impregnation step, and the defect in the surface of the prepreg sheet where the release paper is not present is detected. The apparatus for producing prepreg shown in FIG. 4 is, at least in these points, the same as the apparatus for producing prepreg shown in FIG. 3.

The apparatus for producing prepreg shown in FIG. 4 is different from the apparatus for producing prepreg shown in FIG. 3 in that the defect in the surface of a resin film of a resin sheet introduced into the second resin impregnation step in the apparatus for producing prepreg shown in FIG. 4 is detected. Accordingly, the same steps and apparatus configurations between the apparatus for producing prepreg shown in FIG. 4 and the apparatus for producing prepreg shown in FIG. 3 are designated by the same reference signs in the drawings. Further, descriptions of the steps and apparatus configurations in FIG. 4 designated by the same reference signs as in FIG. 3 are omitted to avoid duplication of the description.

In the apparatus for producing prepreg shown in FIG. 4, a resin sheet inspection step S6A for detecting the defect in the surface of the resin film 6A of the resin sheet 3A moving toward the second resin impregnation step S4b is provided. In the resin inspection step S6A, an optical device OPA4 opposed to the surface of the resin film 6A is provided. The optical device OPA4 is the same as the optical device OPA1 for detecting a defect in the surface of the resin film 6a used in the apparatus for producing prepreg shown in FIG. 1. An object and a function of the optical device OPA4 are the same as those of the optical device OPA1.

In the apparatus for producing prepreg shown in FIG. 4, as with the apparatus for producing prepreg shown in FIG. 3, a marking apparatus 12a is installed at a position prior to the prepreg sheet taking-up apparatus 10A. Information on the defects, which is detected and identified before reaching the marking apparatus 12a, is marked on the release paper 5A of the prepreg sheet 9a by the marking apparatus 12a. Although information on the defects in both surfaces of the prepreg sheet 9 and the prepreg sheet 9a is marked by the marking apparatus 12a, information on the defects in either one surface alone may be marked depending on the situation.

In marking, it is preferred to appropriately select a color or a shape of the mark, and mark a defect at a position of defect occurrence, for example, a defect detected at the surface or the back surface of a prepreg sheet after the first impregnation step and prior to the second impregnation step, a defect detected at the surface of the resin film moving toward the second impregnation step, and a defect detected at the surface of the prepreg sheet after the second impregnation step. Also, it is preferred to mark a mark according to the type of defect.

The position at which a mark is marked is preferably a position inward at a predetermined distance from an end of the release paper on the back surface of the prepreg sheet. The distance is more preferably about 6 to 21 mm from the end face. By setting the lower limit of the distance to 6 mm, improper marking outside of the release paper can be prevented, and by setting the upper limit of the distance to 21 mm, improper marking on the prepreg can be prevented. The marking apparatus 12a is not particularly limited as long as it can mark on the release paper, but a pen-type marking apparatus is preferably used. Further, the marking of a defect name is effective particularly for improving inspection efficiency in a subsequent step.

When the defect intermittently occurs, a mark is preferably marked at a release paper area (usually, referred to as an ear area) on a side end side of the prepreg sheet of an occurrence point, and when the defect occurs continuously, the mark is preferably marked at a release paper area on a side end side of the prepreg sheet of an end point of the defect occurrence. Thereby, workability at the time of inspection can be improved. Moreover, in order to distinguish the defect continuously occurring from the defect intermittently occurring, it is preferred to vary the length of the mark or vary the type or color of the line. In the case of the defect continuously occurring, the mark may be marked over the whole section throughout which the defect is present.

The prepreg sheet roll 10b taken up by the prepreg sheet taking-up apparatus 10A is sorted out together with the position information of the defect, preferably together with the type information of the defect by the prepreg sheet roll, and transferred to the prepreg sheet inspection step S7a which is a step next to the production step of the prepreg. In the prepreg sheet inspection step S7a, the surface of the prepreg sheet 9a wound off from the winding-off apparatus 21a is inspected by the inspector 22a, and taken up around the taking-up apparatus 23a for products.

In performing inspection, it is preferred to enable confirmation of the defect by a means for arithmetically computing a position where the defect (a marked part when marking is performed) detected in the prepreg sheet production step appears in the inspection step from position information of the defect, and actuating an alarm device 24a to give an alarm, and/or decreasing the moving speed of the prepreg sheet in the inspection step when the position appears in the inspection step. By applying such a means, the inspector 22a can identify the position of the defect in the front surface and the back surface of the prepreg sheet precisely, and prevent missing of the defect, decrease the difficulty level of the inspection operation, and improve working efficiency.

In rolling up the prepreg sheet, an end product, by the taking-up apparatus 23a, a so-called splice treatment, in which a defect area is eliminated and normal areas are bound together, is performed according to a treatment criterion peculiar to the kind of the product, or reworks such as elimination of the carbon fiber fuzz defect, the carbon fiber bundle gap defect or the foreign matter contamination defect, which can be reworked, or a work of attaching a tag is performed according to a criterion. By inputting information on these works into a production information management system and performing arithmetic computation using necessary position information of the defect in addition to previous information, the defect information on the product after the inspection is preferably compiled. It is moreover preferred that the information is used as the defect information of a product after going through required certification.

The prepreg sheet inspection step S7a may include a so-called trimming step in which both ends of the prepreg sheet are slit, a step of slitting a prepreg sheet into a width of 2 to 600 mm in a longitudinal direction during inspection so that wide prepreg can be used in an automatic tape laminating machine or an automatic fiber placement machine. Further, it is also preferred that a defect inspection apparatus similar to the above-mentioned defect inspection apparatus but not shown in FIG. 4, is placed in the inspection step to detect the defect.

In the apparatus for producing prepreg shown in FIG. 3 or FIG. 4, two resin impregnation steps of impregnating the resin into the carbon fiber bundle are provided, and sometimes the number of the resin impregnation steps is increased as required. When the resin impregnation step has two stages, the surface of the prepreg sheet is covered with a resin after a second resin impregnation step to make a difference between projections and depressions of the surface small, and the detection of the carbon fiber fuzz defect may become difficult. In such a case, it is preferred to detect the carbon fiber fuzz defect between the first resin impregnation step and the second resin impregnation step. With respect to the carbon fiber bundle gap defect, since a detection signal thereof is emphasized by the existence of a release paper on the back surface of the prepreg sheet, it is preferred to detect the carbon fiber bundle gap defect in the surface of prepreg sheet which has passed through the last resin impregnation step and is in the way to the taking-up apparatus.

Further, other defects present at the back surface of the prepreg sheet need to be inspected for the prepreg sheet in a state in which the release paper is not present at the surface between the front and rear resin impregnation steps since the release paper is present at the back surface of the prepreg sheet having passed through the last resin impregnation step.

In the case where the resin is impregnated into the carbon fiber bundle in two or more stages, when the defect in the surface of the prepreg sheet having passed through all the resin impregnation steps is inspected, it is preferred to detect the foreign matter contamination defect, the carbon fiber bundle gap defect and the release paper wrinkle defect by receiving the scattered reflected light from the surface of the prepreg sheet by the light receiving apparatus, and it is preferred to detect the streak-like resin missing defect and the spot resin missing defect by receiving the direct reflected light from the surface of the prepreg sheet by the light receiving apparatus. As described above, since the state of the prepreg sheet varies depending on the position of defect detection, it is preferred to appropriately selectively use the direct reflected light and the scattered reflected light according to the detection position and the defect type so that the S/N ratio of the defect area can increase.

The width of the prepreg sheet produced by the method of producing prepreg of the present invention is not particularly limited, and the width is preferably 500 to 2000 mm. Particularly in the case of a prepreg sheet having a width of 600 mm or more, the accuracy of defect detection is excellent compared with visual defect detection by an inspector, and prepreg of high quality can be produced.

The production speed of a prepreg sheet in the method of producing prepreg of the present invention is not particularly limited, and the production speed is preferably 1 to 30 m/rain. The carbon fiber bundle to be used is not particularly limited, but the yield of the carbon fiber bundle is preferably 0.05 to 6 g/m, and more preferably 0.15 to 2 g/m. The carbon fiber bundle preferably has a strength of 3000 MPa or more and a modulus of 200 GPa or more, and more preferably has a strength of 4900 MPa or more and a modulus of 280 to 360 GPa. Since the carbon fiber bundle has a strength of 3000 MPa or more, frequent occurrence of defects such as fuzz can be prevented when prepreg is formed by impregnating a resin. By setting the strength to 4900 MPa or more and setting the temperature and pressure conditions at the time of forming prepreg, the number of fuzz defects, for example, fuzz defects having a diameter of 5 cm or more, can be maintained at a good level, for example, as small as $10/m^2$ or less.

As a resin to be impregnated into the carbon fiber bundle, that is, as a matrix resin, an epoxy resin, a vinyl ester resin, a BMI resin, or a polyimide resin is applied, and among these resins, an epoxy resin composition which is an epoxy-based composition cured at 180° C. and contains an additive emitting fluorescence is preferable, and particularly, a resin composition containing an epoxy resin containing an aromatic amine-based curing agent or an epoxy resin having a six-membered ring is more preferable. A resin in the first resin impregnation has the same basic composition as a resin in the second resin impregnation, and as the resin in the second resin impregnation, a resin that contains a thermoplastic resin or a conductive particle component, which increases interlaminar toughness, and that is provided with additional performance is preferred.

Specific examples of the thermoplastic resin include polyamide 12 particles formed into fine particles, polyamide fine particles (Toraypearl™ produced by Toray Industries, Inc.), polyamideimide, and fine particles of polyetheretherketone, and examples of the conductive particle component include polymer fine particles coated with metal plating for imparting conductivity thereto and carbon black.

The weight per unit area of a carbon fiber of a prepreg sheet in the method of producing prepreg of the present invention is preferably 50 to 300 $g/m^2$, and the weight content percentage of a resin of the prepreg sheet is preferably 25 to 50%.

According to the method of producing prepreg of the present invention, the prepreg can be produced by detecting a defect appearing in the prepreg in the production process of prepreg and using information on the detected defect. Furthermore, the judgment of the type and position of the detected defect is performed based on characteristics of reflected light from the surface of the resin film formed by coating the release paper which is used for impregnating a resin into a carbon fiber bundle with a resin, or based on characteristics of reflected light from the surface of the prepreg sheet formed by impregnating a resin into a carbon fiber bundle, from which the release paper has been separated. Thereby, it becomes possible to identify the defect in the direct surface of the prepreg in which the detection of the defect is heretofore impossible since the release paper is present, and it becomes possible to produce prepreg of high quality.

DESCRIPTION OF REFERENCE SIGNS

1: Carbon fiber bundle
1a: Bobbin
2: Carbon fiber sheet
3A, 3B, 3a, 3b: Resin sheet
4a, 4b: Resin sheet roll
5A, 5B, 5a, 5b: Release paper
6A, 6B, 6a, 6b: Resin film
7, 7a, 7b: Laminated sheet
8a, 8b: Heater
9, 9a: Prepreg sheet
10, 10A: Prepreg sheet taking-up apparatus
10a, 10b: Prepreg sheet roll
11B, 11a, 11b: Release paper taking-up apparatus
12, 12a: Marking apparatus
21, 21a: Winding-off apparatus
22, 22a: Inspector
23, 23a: Taking-up apparatus
24, 24a: Alarm device
31: Light irradiation apparatus
31a, 31b: Light source
32: Light receiving apparatus
32a: Camera
32b: Optical filter
33: Defect judgment apparatus
41A, 41B: Light irradiation apparatus
41a, 41b: Light source
42A, 42B: Light receiving apparatus
43A, 43B: Defect judgment apparatus
GR: Guide roll
OPA1, OPA2A, OPA2B, OPA3, OPA4: Optical device
PL1, PL2, PL3: Prepreg sheet production line
S1: Carbon fiber sheet supply step
S2A, S2B, S2a, S2b: Resin sheet supply step
S3, S3a: Laminated sheet forming step
S4: Resin impregnation step
S4a: First resin impregnation step
S4b: Second resin impregnation step
S5, S5a: Prepreg sheet taking-up step
S6, S6A: Resin sheet inspection step S7, S7a: Prepreg sheet inspection step
S8, S8a: Defect information output step
S9: Prepreg sheet inspection step
S10: Prepreg sheet inspection step
θa, θb: Incident angle
θc: Camera installation angle

The invention claimed is:

1. A method of producing prepreg, comprising:
   (a) at least one resin sheet supply step of continuously supplying a resin sheet made of a release paper and a resin film formed from a resin coated the release paper,
   (b) a carbon fiber sheet supply step of continuously supplying a carbon fiber sheet formed of a carbon fiber bundle, or a carbon fiber bundle impregnated with a resin,
   (c) a laminated sheet forming step of opposing the surface of the resin film supplied from the resin sheet supply step to at least one surface of the carbon fiber sheet supplied from the carbon fiber sheet supply step to form a laminated sheet including the resin sheet and the carbon fiber sheet,
   (d) at least one resin impregnation step of impregnating the resin in the laminated sheet in the carbon fiber bundle into the laminated sheet formed in the laminated sheet forming step to form a prepreg sheet including the carbon fiber bundle and the resin impregnated into the carbon fiber bundle, and
   (e) a prepreg sheet taking-up step of continuously taking up the prepreg sheet formed in the resin impregnation step, wherein the method of producing prepreg comprises
   (g) at least one prepreg sheet inspection step of detecting a defect in the surface of the prepreg by inspecting the surface of the prepreg sheet with an optical device after separating the release paper from the prepreg sheet with the release paper including the release paper, which is derived from the resin impregnation step, and judging which of a carbon fiber fuzz defect, a foreign matter contamination defect, a carbon fiber bundle gap defect, a release paper wrinkle defect, a streak-like resin missing defect, and a spot resin missing defect the detected defect belongs to,
wherein the optical device in the prepreg sheet inspection step comprises a light irradiation apparatus for irradiating the surface inspected for the defect with light, a light receiving apparatus for detecting reflected light from the surface of light emitted from the light irradiation apparatus, and a defect judgment apparatus for comparing an intensity value of the reflected light detected by the light receiving apparatus with a threshold value previously set to detect the defect and judging which of a carbon fiber fuzz defect, a foreign matter contamination defect, a carbon fiber bundle gap defect, a release paper wrinkle defect, a streak-like resin missing defect, and a spot resin missing defect the defect belongs to;
wherein the defect judgment apparatus previously sets a threshold value of at least one selected from the group consisting of brightness, width, length and area in each of signals of direct reflected light and signals of scattered reflected light for each of the carbon fiber fuzz defect, the foreign matter contamination defect, the carbon fiber bundle gap defect, the release paper wrinkle defect, the streak-like resin missing defect and the spot resin missing defect, determines the type of the reflected light to be used for detection based on the sensitivity of each reflected light for every defect, and classifies the detected defect into each defect by comparing these threshold values with the signals of the reflected light; and
wherein the resin sheet supply step is provided on both sides of the carbon fiber sheet supplied by the carbon fiber sheet supply step with the carbon fiber sheet sandwiched between the resin sheet supply steps, a plurality of the resin sheet supply steps are provided between the carbon fiber sheet supply step and the prepreg sheet taking-up step, and one of the release papers positioned at both outer surfaces of the prepreg sheet having passed through the resin impregnation step positioned at a position closest to the prepreg sheet taking-up step is separated, the prepreg sheet with the release paper, to which the other release paper adheres, is taken up by the prepreg sheet taking-up step, and the defect in the surface of the prepreg sheet, from which the one release paper has been separated, is inspected by the prepreg sheet inspection step.

2. The method of producing prepreg according to claim 1, wherein the defect judgment apparatus classifies the defect into the carbon fiber fuzz defect, the carbon fiber bundle gap defect, the release paper wrinkle defect, the streak-like resin missing defect or the spot resin missing defect based on detected direct reflected light, and classifies the defect into the foreign matter contamination defect based on detected scattered reflected light.

3. The method of producing prepreg according to claim 1, wherein the resin sheet supply step is provided on both sides of the carbon fiber sheet supplied by the carbon fiber sheet supply step with the carbon fiber sheet sandwiched between the resin sheet supply steps, and the detection of the defect in the surface of the prepreg sheet in the prepreg sheet inspection step is performed by the optical devices installed for both the surfaces of the prepreg sheet.

4. The method of producing prepreg according to claim 1, wherein the optical device in the prepreg sheet inspection step comprises a light irradiation apparatus for irradiating the surface inspected for the defect with light, a light receiving apparatus for detecting reflected light from the surface of light emitted from the light irradiation apparatus, and a defect judgment apparatus for comparing an intensity value of the reflected light detected by the light receiving apparatus with a threshold value previously set to detect the defect and judging which of a foreign matter contamination defect, a carbon fiber bundle gap defect, a release paper wrinkle defect, a streak-like resin missing defect, and a spot resin missing defect the defect belongs to, wherein the defect judgment apparatus classifies the defect into the foreign matter contamination defect, the carbon fiber bundle gap defect or the release paper wrinkle defect based on detected scattered reflected light, and classifies the defect into the streak-like resin missing defect or the spot resin missing defect based on detected direct reflected light.

5. The method of producing prepreg according to claim 1, wherein the light irradiation apparatus in the prepreg sheet inspection step is a light irradiation apparatus of linear LED light, and the light receiving apparatus is a light receiving apparatus including a CCD line sensor camera.

6. The method of producing prepreg according to claim 1, wherein a position of the defect detected in the prepreg sheet inspection step relative to the prepreg sheet is marked by a marking apparatus at a predetermined position at an end in a width direction of the release paper of the prepreg sheet taken up together with the release paper in the prepreg sheet taking-up step, and the type of the defect and the position of the defect in the prepreg sheet are determined by the marking.

7. The method of producing prepreg according to claim 1, further comprising a second prepreg sheet inspection step provided posterior to the prepreg sheet taking-up step, wherein the second prepreg sheet inspection step has a defect information output step which transfers position information of the defect detected in the prepreg sheet inspection step, or the position information and the type information of the defect to the second prepreg sheet inspection step, identifies a position of the defect in the second prepreg sheet inspection step by performing arithmetic computations using information on work in process in the second prepreg sheet inspection step, and gives an alarm and/or decreases a moving speed of the prepreg sheet in the second prepreg sheet inspection step when the defect appears in the second prepreg sheet inspection step to enable confirmation of the defect, and outputs, as inspection results, defect information into which position information of the defect or position information and type information of the defect, and defect information and position information, respectively verified in the second prepreg sheet inspection step, are consolidated.

8. The method of producing prepreg according to claim 7, wherein the defect area is eliminated or a sign is attached to the defect area according to treatment criteria of products previously set based on the confirmation of the defect.

* * * * *